United States Patent
Yokobayashi et al.

(10) Patent No.: US 8,848,193 B2
(45) Date of Patent: Sep. 30, 2014

(54) NON-DESTRUCTIVE INSPECTION DEVICE FOR OXYGEN CONCENTRATION IN BAG-SHAPED CONTAINER

(75) Inventors: Takayasu Yokobayashi, Osaka (JP); Yoshinari Horimoto, Osaka (JP)

(73) Assignee: Hitachi Zosen Corporation, Osaka (JP)

( * ) Notice: Subject to any disclaimer, the term of this patent is extended or adjusted under 35 U.S.C. 154(b) by 0 days.

(21) Appl. No.: 14/112,274

(22) PCT Filed: Apr. 13, 2012

(86) PCT No.: PCT/JP2012/060101
§ 371 (c)(1),
(2), (4) Date: Oct. 17, 2013

(87) PCT Pub. No.: WO2012/147537
PCT Pub. Date: Nov. 1, 2012

(65) Prior Publication Data
US 2014/0029007 A1    Jan. 30, 2014

(30) Foreign Application Priority Data

Apr. 28, 2011   (JP) .................................. 2011-100289

(51) Int. Cl.
| | | |
|---|---|---|
| G01N 21/00 | (2006.01) | |
| G01N 21/27 | (2006.01) | |
| G01N 21/90 | (2006.01) | |
| G01N 21/01 | (2006.01) | |
| G01N 21/35 | (2014.01) | |
| G01N 21/59 | (2006.01) | |

(52) U.S. Cl.
CPC ...... *G01N 21/59* (2013.01); *G01N 2201/06113* (2013.01); *G01N 21/278* (2013.01); *G01N 21/90* (2013.01); *G01N 21/01* (2013.01); *G01N 2021/0187* (2013.01); *G01N 21/3504* (2013.01)

USPC ............................................. 356/437; 356/440

(58) Field of Classification Search
USPC ................................................. 356/432–442
See application file for complete search history.

(56) References Cited

U.S. PATENT DOCUMENTS

| 7,067,323 B2 | 6/2006 | Veale et al. ............... 436/136 |
| 8,379,209 B2 | 2/2013 | Yokobayashi et al. ....... 356/437 |

FOREIGN PATENT DOCUMENTS

| JP | 62-206830 | 9/1987 | ............ H01L 21/30 |
| JP | 2005-189196 | 7/2005 | |
| JP | 2007-508567 | 4/2007 | ............ G01N 35/00 |
| JP | 2009-014589 | 1/2009 | ............ G01N 21/59 |
| JP | 2010-38846 | 2/2010 | ............ G01N 21/27 |

OTHER PUBLICATIONS

Int'l Search Report from corresponding PCT/JP2012/060101 (Form PCT/ISA/210); 2 pages.

*Primary Examiner* — Tri T Ton

(74) *Attorney, Agent, or Firm* — Kusner & Jaffe

(57) ABSTRACT

A laser emitting section 59A and a laser receiving section 59B for measuring an oxygen concentration are provided on two sides of an inspection area so as to be moved toward and away from a bag-shaped container 1. Gas-filled chambers 61 provided on the end faces of the laser emitting section 59A and the laser receiving section 59B are brought into contact with the gas phase portion of the container 1 to keep a constant thickness of the gas phase portion. A tilting device 81 is provided to press the container 1, which is held by a container holder 16, from both sides with a container pressing member 88 and tilts the container 1 in a vertical plane. When an oxygen concentration is measured, the tilting device 81 tilts the bag-shaped container 1 to measure the gas phase portion at the shoulders of the container 1.

7 Claims, 15 Drawing Sheets

F I G. 5
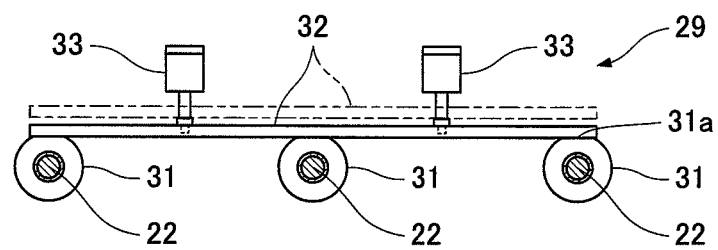

F I G. 1 0
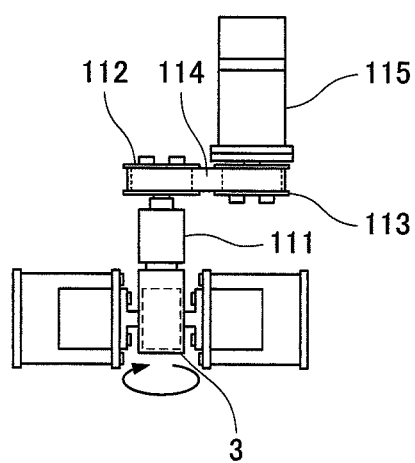
F I G. 1 1
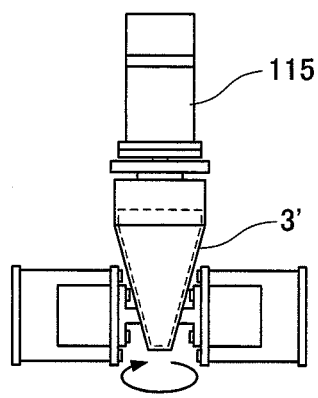

F I G. 1 4
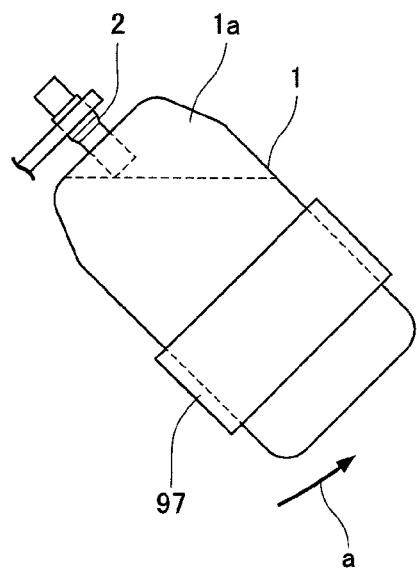
F I G. 1 5
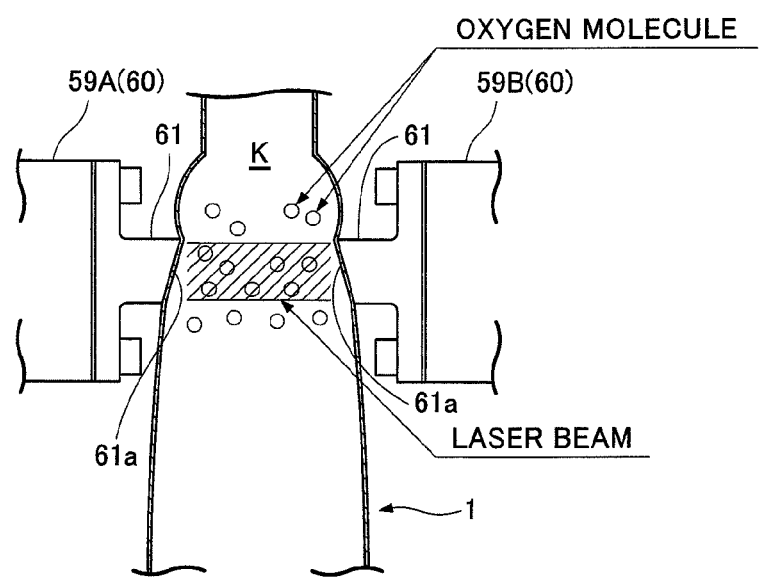

NON-DESTRUCTIVE INSPECTION DEVICE FOR OXYGEN CONCENTRATION IN BAG-SHAPED CONTAINER

TECHNICAL FIELD

The present invention relates to a non-destructive inspection device provided in a liquid filler to inspect an oxygen concentration in a bag-shaped container filled with a liquid.

BACKGROUND ART

Medical infusions are injected into bag-shaped containers, e.g., infusion bags and then are transported and stored.

Such a bag filled with a medical infusion contains nitrogen gas to prevent oxidation and degradation of the infusion. After a bag is filled with an infusion, the oxygen concentration of the infusion is measured to inspect whether the infusion is defective or not. In other words, it is naturally preferable that less oxygen is entrained during manufacturing, and thus when the oxygen concentration is higher than a permissible value, it is decided that the product is defective.

This inspection is conducted by a destructive method in which an injection needle is inserted into a product bag serving as a sample and air is collected to measure the oxygen concentration. After the inspection, the sample is discarded. Since the inspection is not a one hundred percent inspection but a sample inspection, safety and sanitation may not be secured.

For products in vial containers other than products in infusion bags, a method is available in which oxygen entrained or present in a container in the manufacturing process is detected by a laser beam (e.g., it is described in National Publication of International Patent Application No. 2007-508567 (hereinafter, will be referred to as Patent Literature 1)).

Specifically, in this method, a laser beam is transmitted to a gas phase portion on the top of a vial container and the amount of transmitted light is measured. In other words, the absorbance is detected to measure an oxygen concentration.

When an oxygen concentration in a bag is measured by a laser beam, it is necessary to keep constant the transmission distance of the laser beam (different distances naturally cause variations in measured oxygen concentrations).

As described in Patent Literature 1, a vial container is hard and thus a laser beam is transmitted at a constant distance, so that an oxygen concentration can be measured with relatively high accuracy.

However, infusion bags are made of soft materials and vary in thickness, so that non-destructive inspections using laser beams cannot be conducted with high accuracy.

In order to solve the problem, the applicant has proposed a non-destructive inspection device which can accurately inspect an oxygen concentration in a bag-shaped container filled with a liquid, by using a laser beam in a non-destructive inspection.

The non-destructive inspection device measures an oxygen concentration by emitting a laser beam to a gas phase portion while keeping bag shoulders in a horizontal position (For example, Japanese Patent Laid-Open No. 2010-38846(hereinafter, will be referred to as Patent Literature 2)).

SUMMARY OF INVENTION

Technical Problem

According to the configuration of Patent Literature 2, the bag shoulders are kept in the horizontal position so as to keep a constant thickness of the gas phase portion. The gravity of a hung bag leads to a small thickness of the gas phase portion in the upper part of the bag and reduces the horizontal section of the gas phase portion toward the end of the bag. This leads to a small distance between a laser emitting section and a laser receiving section that hold the bag from two sides of the gas phase portion, causing difficulty in measurement.

An object of the present invention is to provide a non-destructive inspection device which is easy to measure when accurately inspecting an oxygen concentration in a bag-shaped container filled with a liquid, by a laser beam in a non-destructive inspection.

Solution to Problem

In order to solve the problem, a first aspect of the present invention is a non-destructive inspection device provided in a liquid filler for feeding a liquid into bag-shaped containers held by container holders on a transport unit and transported along a transport path including at least a liquid filling area, a sealing area, and an inspection area, the non-destructive inspection device emitting, in the inspection area of the transport path, a laser beam to the gas phase portion of the bag-shaped container filled with the liquid and measuring an oxygen concentration in the bag-shaped container based on the amount of transmitted light, the non-destructive inspection device including: a pair of right and left moving members provided on the right and left of the inspection area of the transport path such that the moving members are moved toward and away from the bag-shaped container by a moving device; a laser emitting section that is provided on one of the moving members and emits the laser beam for measuring the oxygen concentration; and a laser receiving section that is provided on the other moving member and receives the laser beam, wherein the non-destructive inspection device further includes:

translucent inert gas chambers having an equal length on the respective end faces of the laser emitting section and the laser receiving section; and a tilting device that is disposed on the right and left of the inspection area of the transport path so as to press the bag-shaped container from both sides by means of a container pressing member and tilt the container in a vertical plane, the container being held by the container holder so as to pivot in the vertical plane, and in measurement of the oxygen concentration in the inspection area, the tilting device tilts the bag-shaped container to a predetermined angle and brings the pair of right and left moving members close to each other at the shoulders of the upper part of the tilted bag-shaped container so as to bring the end faces of the laser emitting section and the laser receiving section into contact with the surface of the gas phase portion of the bag-shaped container, keeping a constant thickness of the gas phase portion while evacuating air between the end faces of the laser emitting section and the laser receiving section and the surface of the gas phase portion of the bag-shaped container.

According to a second aspect of the present invention, the container pressing member of the non-destructive inspection device includes a vibrator.

According to a third aspect of the present invention, in the non-destructive inspection device, the transport unit is stopped and the pair of moving members having the laser emitting section and the laser receiving section is movable to the stopped bag-shaped containers in the inspections of the bag-shaped containers.

According to a fourth aspect of the present invention, the non-destructive inspection device further includes two calibration containers that are made of a translucent material outside the inspection area and are filled beforehand with inert gas having different oxygen concentrations, wherein the pair of moving members having the laser emitting section and the laser receiving section is movable to calibration positions for measuring the oxygen concentrations in the calibration containers.

According to a fifth aspect of the present invention, the calibration container is conical or cylindrical and is rotatable about the axis of the container, and the transport path is circular or oval.

Advantageous Effects of Invention

According to the configurations, inert gas chambers on the ends of a laser emitting section and a laser receiving section are filled with nitrogen gas. In this state, the gas phase portion of a container is pressed from both sides to a constant thickness by the end faces of the laser emitting section and the laser receiving section, air is removed between the end faces of the laser emitting section and the laser receiving section and the surface of the gas phase portion of the bag-shaped container, and a laser beam is emitted to measure an oxygen concentration. At this point, the container is pressed by a container pressing member and is tilted in a vertical plane, and then the gas phase portion at the shoulders of the tilted container is measured. This can increase the volume of the gas phase portion and move a sufficient amount of oxygen molecules to the shoulders, thereby easily measuring an oxygen concentration with high accuracy.

Moreover, a vibrator that apply vibrations to the bag-shaped container can evenly disperse oxygen molecules in the gas phase portion, achieving stable and uniform measured values even with a low oxygen concentration.

Furthermore, when an inspection tool is calibrated, a cylindrical calibration container is rotated, achieving precise calibration.

BRIEF DESCRIPTION OF DRAWINGS

FIG. 5 is a G-G sectional view of FIG. 4.

FIG. 10 is a plan view showing the layout of a calibration container in the non-destructive inspection device.

FIG. 11 is a plan view showing the layout of a calibration container according to a modification in the non-destructive inspection device.

FIG. 14 is a side view showing a position of a container during an inspection in the non-destructive inspection device.

FIG. 15 is an enlarged cross-sectional view illustrating the principal part of a container in an inspected state of the non-destructive inspection device.

DESCRIPTION OF EMBODIMENTS

Figure 1:
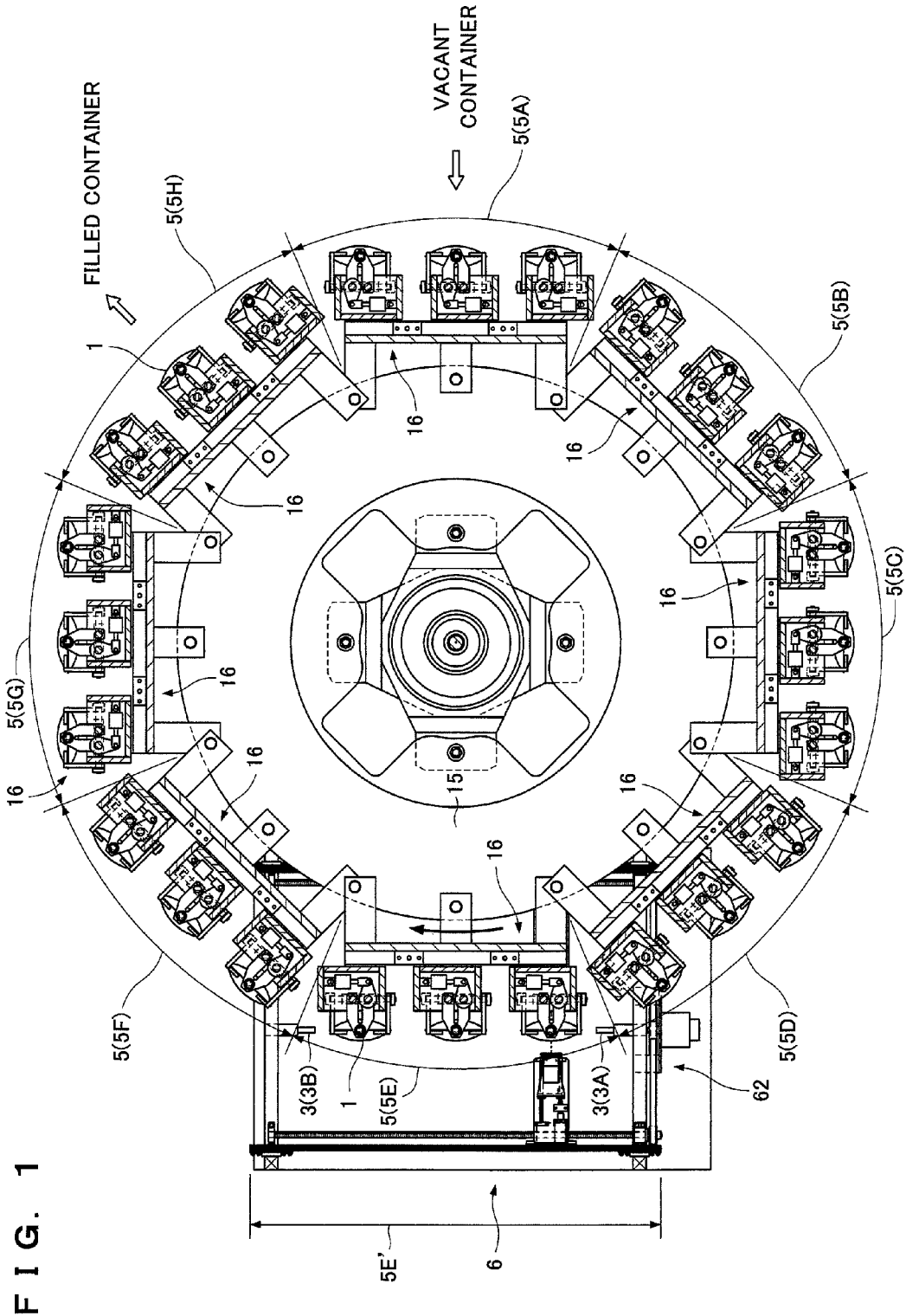
FIG. 1 is a plan view schematically showing the configuration of a liquid filler including a non-destructive inspection device according to an embodiment of the present invention.
Figure 2A:
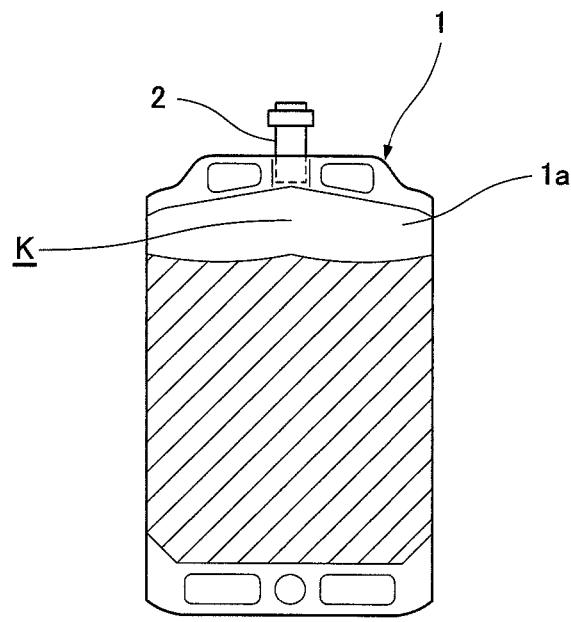
FIG. 2A is a front view showing a bag-shaped container to be inspected by the non-destructive inspection device.
Figure 2B:
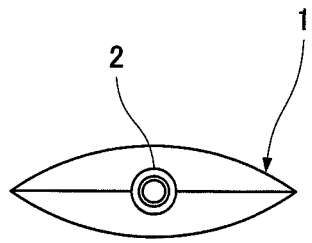
FIG. 2B is a plan view showing the bag-shaped container to be inspected by the non-destructive inspection device.

Referring to FIGS. 1 to 15, the following will describe a non-destructive inspection device for an oxygen concentration in a bag-shaped container according to an embodiment of the present invention.

The non-destructive inspection device is provided in a liquid filler for filling an infusion bag (an example of a bag-shaped container, hereinafter will be called a container), which is made of a soft material (e.g., a soft plastic such as polyolefin), with a medical infusion such as a drip (hereinafter, will be called a liquid). The non-destructive inspection device inspects whether an oxygen concentration is proper or not in a container that is filled with a liquid and has a sealed inlet. Whether an oxygen concentration is proper or not is decided based on the measured value of the oxygen concentration in the container, the oxygen concentration being measured by a laser beam (this measuring method is called, e.g., tunable semiconductor laser absorption spectroscopy).

First, the configuration of the liquid filler will be simply described below.

The liquid filler is a rotary type and, as shown in FIGS. 1 to 4, containers 1 serving as infusion bags are sequentially held and transported along a circular transport path 5; meanwhile, a liquid serving as a medical infusion is injected into the vacant containers 1, inlets 2 of the containers 1 are sealed, it is inspected whether oxygen concentrations in the infusion bags filled with the liquid are proper or not, protective films are applied to the inlets 2, and then the containers 1 are transported to the subsequent process.

The transport path 5 includes: a receiving area 5A (hereinafter, the area will be also called a station) for receiving the containers 1; a gas feeding area 5B for feeding inert gas such as nitrogen gas from the inlets 2 into the containers 1; a liquid feeding area 5C for feeding a liquid from the inlets 2 into the containers 1; a sealing area 5D for capping the inlets 2 of the containers 1 filled with the liquid; an inspection area 5E for inspecting gas phase portions K in the capped containers 1; a film attachment area 5F for attaching protective films to the inlets 2; a defective item ejection area 5G for ejecting a defective item; and a delivery area 5H for delivering the containers 1 to the subsequent process. At positions opposed to the receiving area 5A and the delivery area 5H of the containers 1, container feeding/ejecting machines (not shown) are provided that can feed and eject the containers. In the present embodiment, three of the containers 1 are explained as being intermittently moved each time and are collectively subjected to operations such as injection of a liquid.

The liquid filler holds the containers 1 at predetermined intervals and transports the containers 1 along the circular transport path 5. The liquid filler includes: a pedestal 11; a rotating unit 12 disposed on the pedestal 11; a rotating plate 14 that is connected to a rotating drive shaft 13 disposed perpendicularly to the rotating unit 12 and can be rotated in the horizontal plane; a ring plate (including an inner plate and an outer plate) 15 connected to the outer periphery of the rotating plate 14; and container holders 16 that are disposed at predetermined intervals on the ring plate 15 to hold the containers 1. Further, the rotating unit 12 intermittently rotates the rotating plate 14, that is, the ring plate 15. The rotating unit 12, the rotating drive shaft 13, the rotating plate 14, and the ring plate 15 constitute a transport unit.

The container holder 16 includes: an affixing plate 21 fixed to the ring plate 15; a frame member 23 provided on the affixing plate 21 so as to rotate (tilt) about the horizontal axis via a rotating shaft 22; a pair of rotating shafts 24 (24A, 24B) rotationally held about the vertical axis in the frame member 23; a pair of gears 25 (25A, 25B) that are provided on the respective rotating shafts 24 so as to be engaged with each other; a rotating device such as an opening/closing cylinder (an air or electric cylinder, also in the following explanation in terms of a cylinder) 27 that is connected to one of the rotating shafts 24 (24A) via a connecting arm 26 and oscillates (rotates) the rotating shaft 24A within a predetermined angle range; and a pair of holding arms 28 (28A, 28B) that are respectively attached to the lower ends of the rotating shafts 24 so as to hold and release the inlet 2 of the container 1 from both sides.

Furthermore, a posture fixing device 29 is provided to fix (hold) the rotation angle of the rotating shaft 22, that is, the tilting position of the frame member 23 (that is, the tilting position of the container 1) in the container holder 16. As shown in FIG. 5, the posture fixing device 29 includes approximate circular fixing members 31 fit onto the respective rotating shafts 22, a support plate 32 contactable with flat portions 31a that are the cut portions of the fixing members 31, and lift cylinders 33 that move up or down the support plate 32 so as to move the support plate 32 close to or away from the flat portions 31a. The posture fixing device 29 can simultaneously fix or release the three containers 1. For example, the support plate 32 is moved up or down by the two lift cylinders 33. The lift cylinders 33 are attached to the affixing plate 21.

In the configuration, the opening/closing cylinder 27 is operated to rotate the rotating shaft 24A. At this point in time, the rotating shaft 24B is rotated in the opposite direction via the pair of gears 25 with the same amount of rotation. Thus the inlet 2 of the container 1 can be held and released by the pair of holding arms 28 from both sides. The ends of the holding arms 28 naturally have recessed portions shaped like, e.g., semicircles such that the holding arms 28 can be engaged with the inlet 2.

Near the container holder 16, that is, the frame member 23, a container holder 41 is provided that presses shoulders 1a of the container 1 held by the container holder 16, from the outside to the inside (to be precise, from the outside to the inside of the circular transport path). Thus the container 1 is prevented from vibrating.

Figure 6:
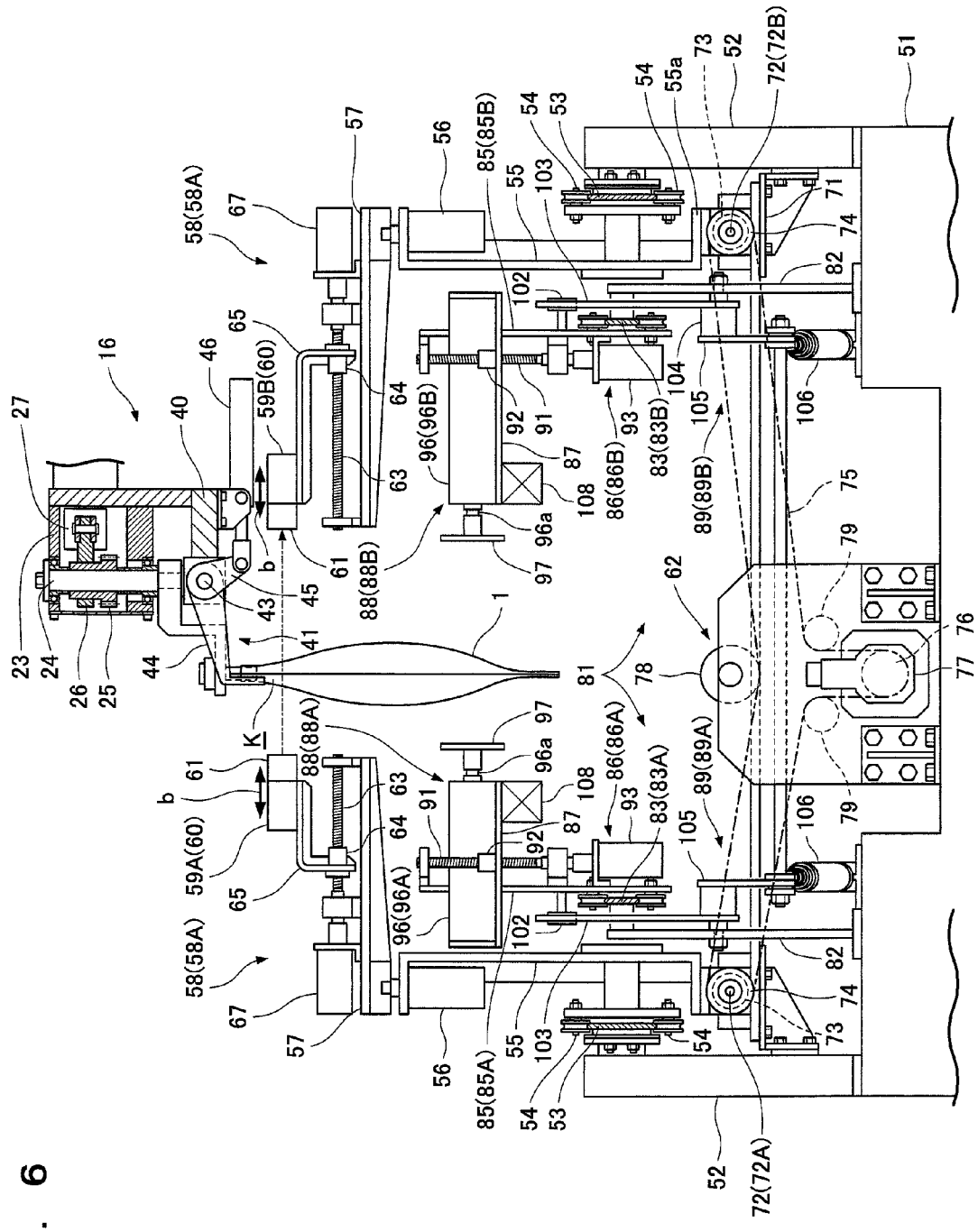
FIG. 6 is a sectional view showing the principle part of the non-destructive inspection device.
Figure 8:
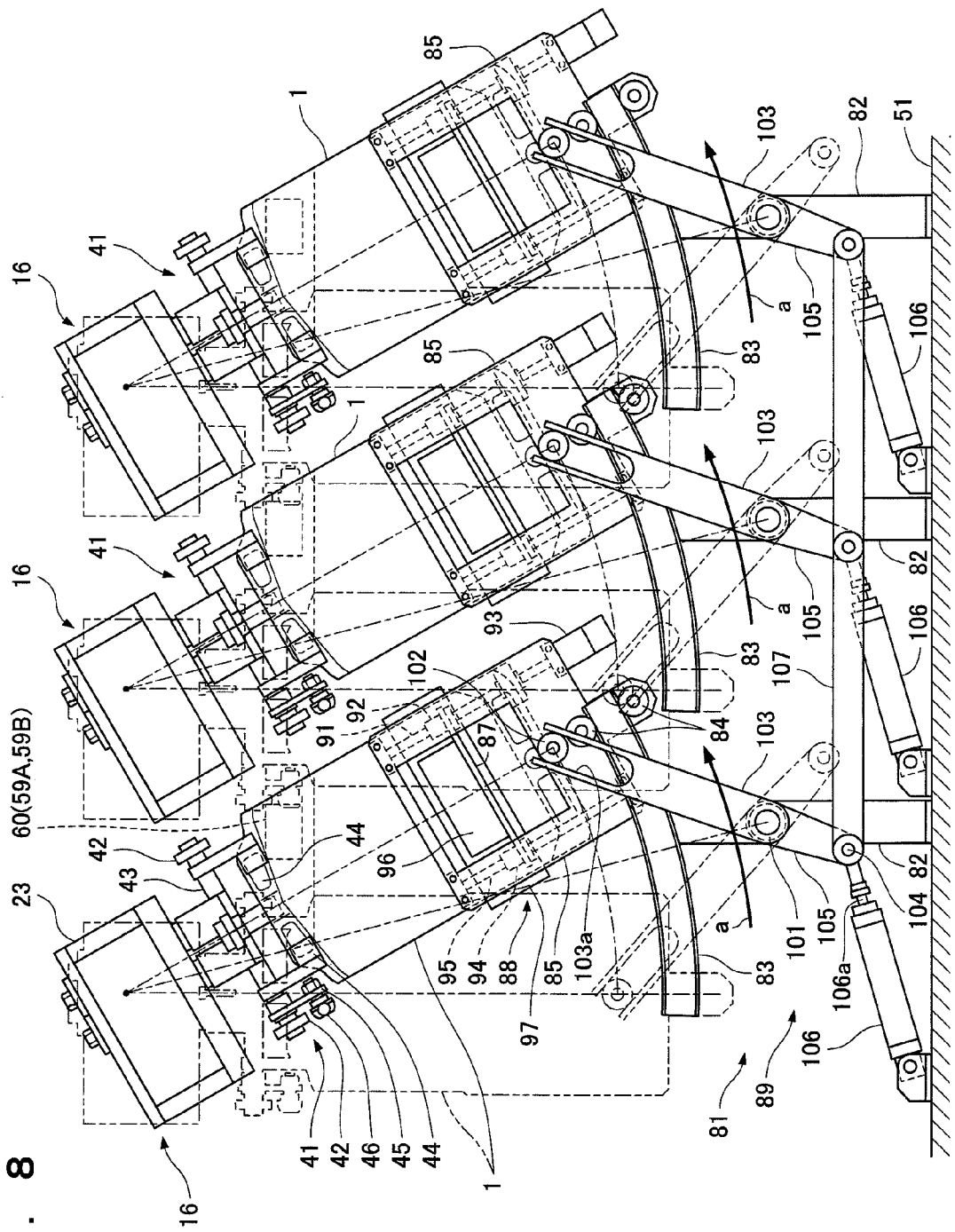
FIG. 8 is an H-H sectional view of FIG. 4.

As shown in FIGS. 6 and 8, the container holder 41 includes: a rotating shaft 43 attached to an attachment bracket 40 provided in the lower end of the frame member 23 via a bearing 42 so as to rotate about a horizontal axis parallel with the width direction of the container 1 (that is, the tangential direction of the transport path); a pair of right and left pressing arms 44 fixed, on the rotating shaft 43, at positions on the shoulders 1a of the container 1; and an oscillation cylinder 46 that is supported by the attachment bracket 40 and oscillates the rotating shaft 43 via a connecting lever 45 by a predetermined angle.

Figure 4:
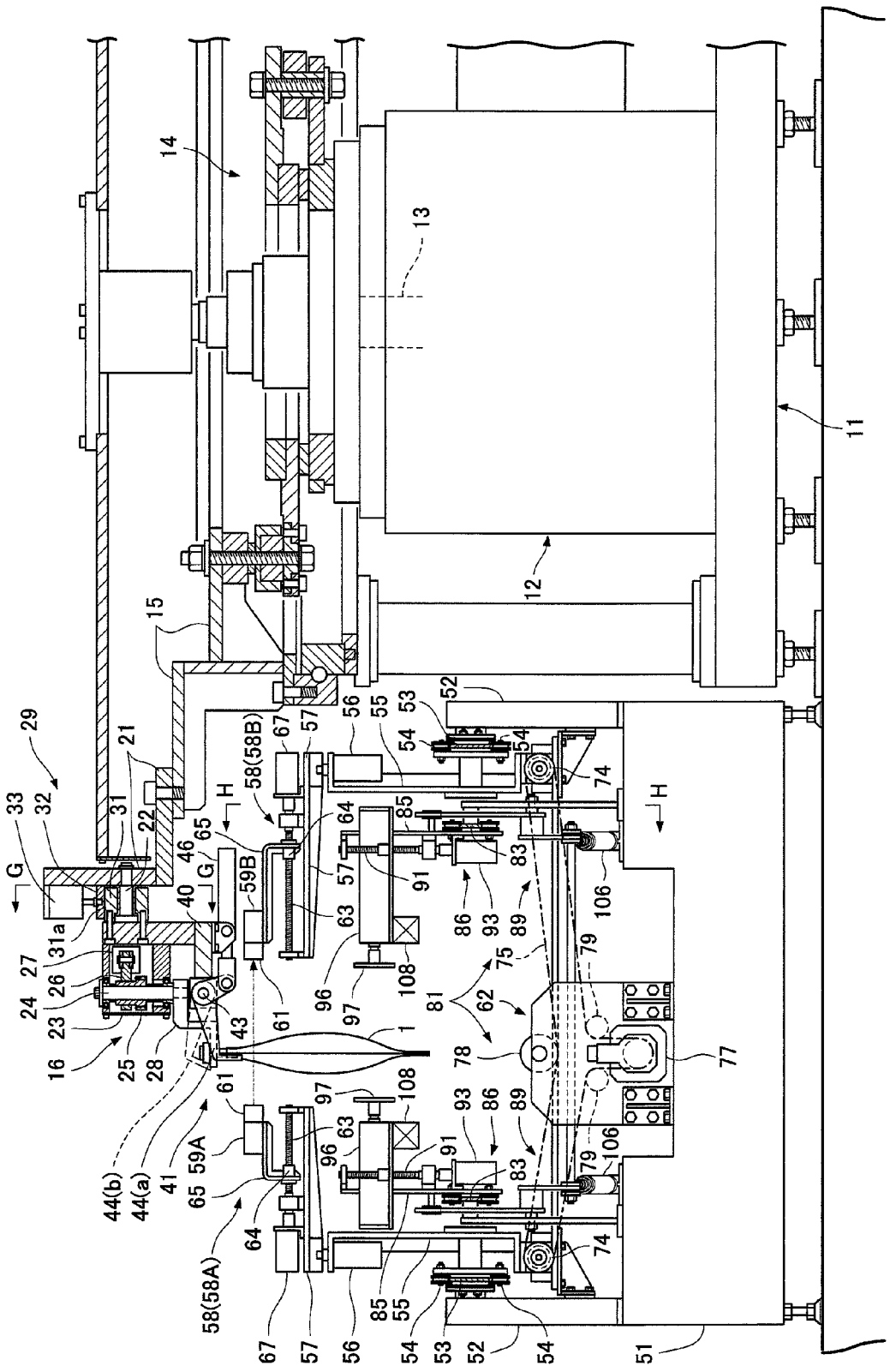
FIG. 4 is an F-F sectional view of FIG. 3.

In this configuration, the operated oscillation cylinder 46 rotates the rotating shaft 43 within a predetermined angle range. To be specific, as shown in FIG. 4, the rotating shaft 43 is oscillated between pressing position (a) where the pressing arms 44 press the surface of the container 1 from the outside to the inside and release position (b) where the pressing arms 44 are separated from the surface of the container 1.

Further, in the inspection area 5E of the transport path 5, a non-destructive inspection device 6 of the present invention is provided.

During this inspection, the transportation of the containers 1 is stopped and the three containers 1 are sequentially inspected during the single stopping operation. Thus the inspection area 5E is longer than the total length of the three containers 1 held by the container holders 16. Outside the three containers 1, calibration containers (will be described later) 3 are provided for the calibration of the inspection device. The inspection area 5E and the calibration containers constitute an inspection/calibration area 5E'.

Based on the explanation, the non-destructive inspection device 6 will be described below.

As shown in FIGS. 3 to 9 (particularly FIGS. 4, 6, and 7), the non-destructive inspection device 6 includes: a support pedestal 51 that is rectangular in plan view in the inspection area 5E having a predetermined length and is provided over the predetermined length at the bottom of the device; a pair of right and left guide members, e.g., guide rails 53 horizontally supported by multiple support members 52 raised on the right and left sides of the support pedestal 51; moving plates 55 movably provided on the respective guide rails 53 via guide wheels 54; lift plates 57 provided on the moving plates 55 so as to move up and down via lift cylinders 56; a laser emitting section 59A that can be moved in an approaching/separating direction b with respect to the container 1 by moving devices 58 (58A, 58B) provided on the lift plates 57 and emits an inspection laser beam or a laser receiving section 59B for receiving the inspection laser beam; gas-filled chambers 61 that are respectively provided at the fronts of the laser emitting section 59A and the laser receiving section 59B and have gas chambers (inert gas chambers) made of a translucent material and filled with nitrogen gas; and a moving device 62 for simultaneously moving the right and left moving plates 55 in the inspection/calibration area 5E'. Specifically, as shown in FIG. 15, the gas-filled chamber 61 has an end face 61a in contact with the container 1. The end face 61a is tilted (or curved) along the surface shape of the container 1 during measurement.

Figure 7:
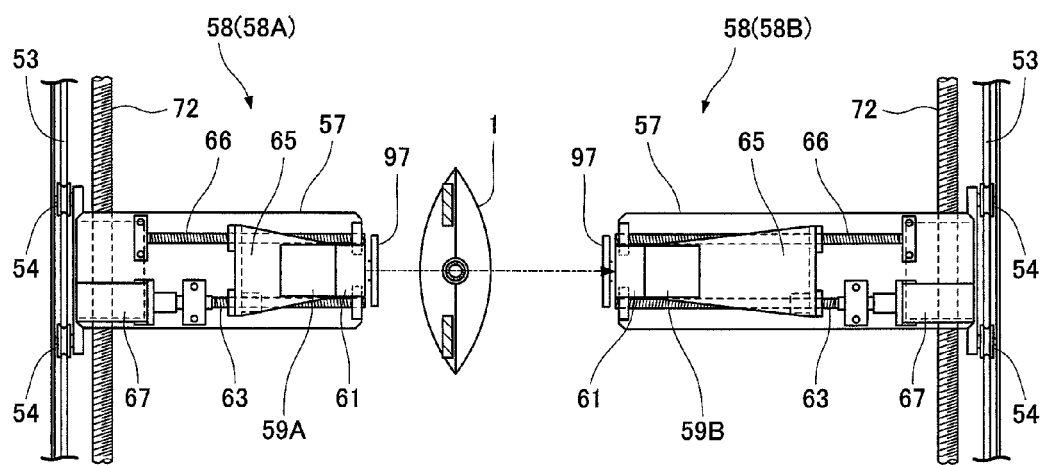
FIG. 7 is a plan view showing the principle part of the non-destructive inspection device.

As shown in FIGS. 6 and 7, the moving device 58 includes: a rotary screw shaft 63 provided on the lift plate 57 in the approaching/separating direction (horizontal direction) b with respect to the container 1 so as to rotate about the axis of the rotary screw shaft 63; a nut member (ball screw mechanism) 64 screwed onto the rotary screw shaft 63; a moving member 65 that has its proximal end attached to the nut member 64 and its front end disposed on the laser emitting section 59A or the laser receiving section 59B and is guided by, for example, a guide rod 66 so as to move only in the approaching/separating direction b; and a motor 67 that rotates the rotary screw shaft 63. The rotary screw shafts 63 in a pair are disposed on the respective lift plates 57.

Of the right and left moving members 65, for example, the left moving member 65 in FIGS. 4 and 6 has the laser emitting section 59A and the right moving member 65 has the laser receiving section 59B. As a matter of course, the positions of the laser emitting section 59A and the laser receiving section 59B may be switched. The laser emitting section 59A and the laser receiving section 59B may be collectively called an inspection tool 60.

The moving device 62 includes: rotary screw shafts 72 (72A, 72B) respectively supported via brackets 71 between the right and left support members 52; nut members (a ball screw mechanism is used) 73 that are screwed onto the rotary screw shafts 72 and are respectively connected to lower-end bending portions 55a of the moving plates 55; driven-side sprockets 74 respectively attached to the ends of the right and left rotary screw shafts 72; and an electric motor 77 that rotates a driving-side sprocket 76 engaged with a transmission belt 75 wound around the driven-side sprockets 74. At an intermediate point of the transmission belt 75, a sprocket 78 is provided for pressing the transmission belt and sprockets 79 are provided for tensing the transmission belt.

In this configuration, when the electric motor 77 is driven to rotate the rotary screw shafts 72, the right and left moving plates 55, that is, the laser emitting section 59A and the laser receiving section 59B are simultaneously moved to the stop positions of the three containers 1, that is, first inspection position (A), second inspection position (B), and third inspection position (C) and to the positions of the two calibration containers 3 outside the three containers 1, that is, first calibration position (D) and second calibration position (E).

The non-destructive inspection device 6 includes a tilting device 81 for the container 1. The tilting device 81 tilts the container 1 and gathers air in the above shoulders 1a to obtain a sufficient thickness of the gas phase portion K during measurement using a laser beam, achieving accurate measurement of an oxygen concentration with a laser beam.

As shown in FIGS. 6 and 8, the tilting device 81 includes: three arc-shaped guide rails 83 (83A, 83B) that are provided on support brackets 82 in a longitudinal direction (the transport direction of the container 1), the support brackets 82 being raised on the right and left of the support pedestal 51; tilted plates 85 (85A, 85B) each of which is guided by the guide rail 83 via a pair of guide wheels 84 vertically holding the guide rail 83; a lift plate 87 provided on the tilted plate 85 so as to move up and down via a lifting device 86 (86A, 86B); a container pressing member 88 (88A, 88B) provided on the lift plate 87; and a tilting device 89 (89A, 89B) that moves the tilted plate 85 in a tilted manner along the guide rail 83.

The lifting device 86 includes: a rotary screw shaft 91 vertically rotationally provided on the tilted plate 85; a nut member 92 that is provided on the lift plate 87 and is screwed onto the rotary screw shaft 91; a pair of motors 93 each of which rotates the rotary screw shaft 91; and a guide rod 95 that is provided on the tilted plate 85 and guides the lift plate 87 by means of a cylindrical member 94 provided on the lift plate 87.

The container pressing member 88 includes a container pressing cylinder 96 (96A, 96B) oriented orthogonal to the transport path 5 of the container 1, and a pressing plate 97 that is provided on the end of a rod portion 96a of the container pressing cylinder 96 so as to press the side of the container 1.

The tilting device 89 includes: tilting levers 103 each of which is provided so as to pivot via a support pin 101 in a vertical plane on the support bracket 82 and has a guide groove 103a on the upper end of the tilting lever 103, the guide groove 103a being capable of engaging with an engaging roller 102 provided on the tilted plate 85; and tilting cylinders 106 each of which is connected to the lower end of the tilting lever 103 via a connecting member 104 and a connecting lever 105. The three tilting levers 103 are connected to one another via a connecting rod 107 so as to tilt at the same time.

Thus, the motor 93 of the lifting device 86 is driven to move up and down the pressing plate 97 provided on the lift plate 87, adjusting the pressing position of the container 1.

The rod portions 96a of the right and left container pressing cylinders 96 are projected so as to press the container 1 from both sides with the right and left pressing plates 97. In this state, the rod portions 106a of the tilting cylinders 106 are projected, allowing the tilting levers 103 to tilt in a predetermined direction a so as to tilt the container 1 to a predetermined angle.

For example, the container 1 is tilted to an angle from 30° to 40°. This gathers air in the shoulders 1a so as to increase the thickness of the gas phase portion K. In other words, the gas phase portion K contains a large number of oxygen molecules, facilitating measurement of an oxygen concentration while hardly causing an error.

Furthermore, a vibrator 108 is provided near the container pressing member 88, that is, under the lift plate 87. The vibrator 108 vibrates the container 1 pressed (held) by the pressing plate 97, moving air, e.g., oxygen upward in the liquid phase of the container 1 so as to obtain higher measuring accuracy.

The vibrator 108 vibrating the container 1 evenly disperses oxygen molecules in the gas phase portion, achieving stable and uniform measured values even with a low oxygen concentration.

The vibrator 108 is, for example, an air driven or electrically driven type.

The calibration containers 3 will be described below.

As has been discussed, the calibration containers 3 are disposed on two ends of the support pedestal 51, that is, at the front and the rear of the support pedestal 51. The calibration containers 3 are shaped like cylinders (boxes) composed of a translucent material (e.g., an acrylic sheet) and are rotatable about the horizontal axes.

As shown in FIG. 10, the calibration container 3 is supported near the support pedestal 51 via a support member 111 or the like so as to rotate about the horizontal axis. The support shaft of the calibration container 3 is connected to a motor 115 via a pair of pulleys 112 and 113 and a transmission belt 114. The support shaft is, for example, rotated at 5 to 10 rpm during calibration. As shown in FIG. 11, a calibration container 3' may have a conical shape identical to the surface shape of the shoulders 1a of the container 1. Alternatively, the calibration container 3 may be directly rotated by the motor 115 without using a pulley or a transmission belt. As a matter of course, the conical shape of the calibration container 3' changes with the thickness of the shoulders 1a of the container 1.

Figure 3:
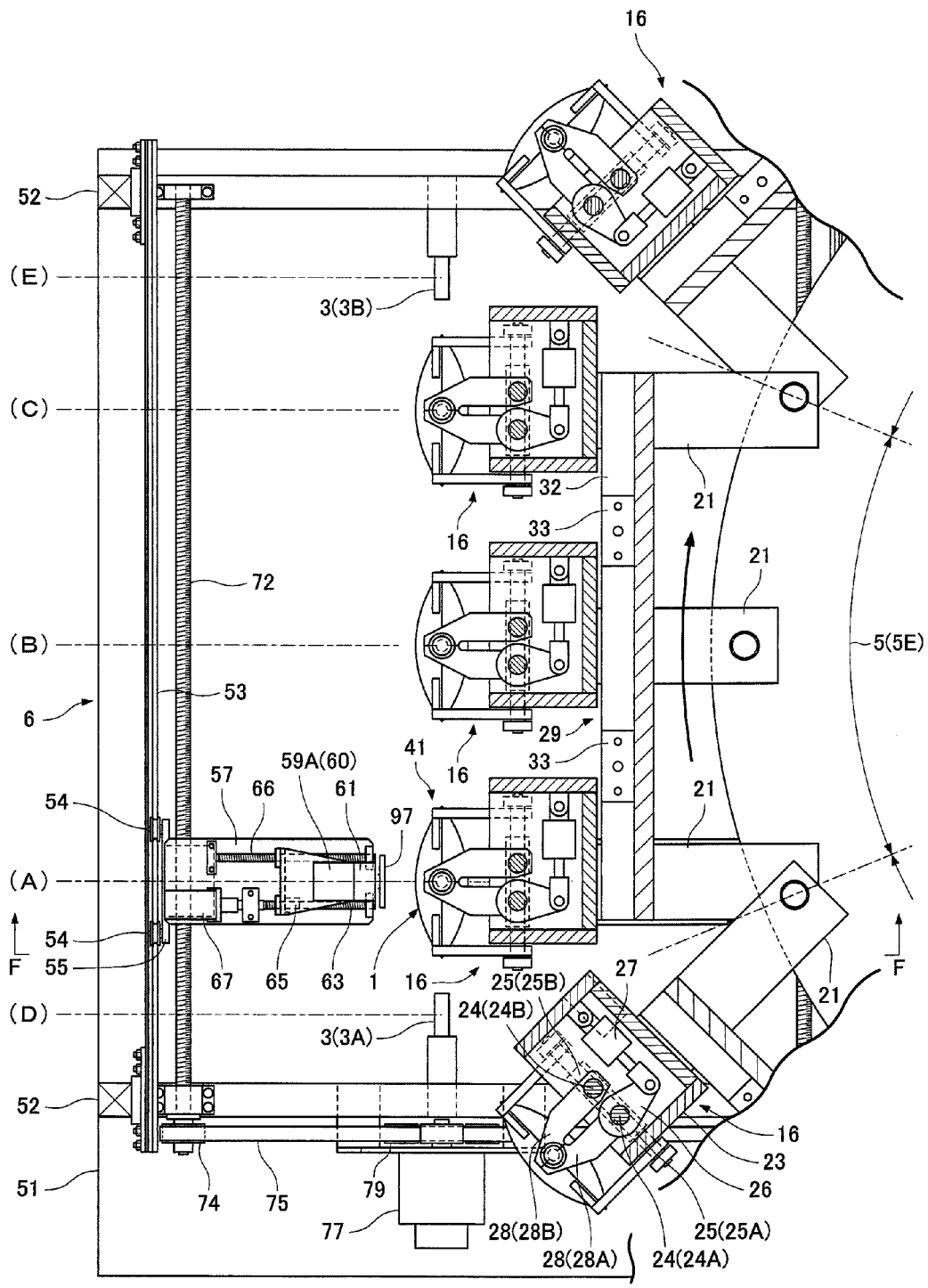
FIG. 3 is a plan view showing the principle part of the non-destructive inspection device.

The calibration container 3 is filled with nitrogen gas serving as inert gas having a predetermined oxygen concentration. For example, as shown in FIGS. 1 and 3, the calibration container 3A has an oxygen concentration of 0% and the calibration container 3B has an oxygen concentration of 20%.

Figure 12:
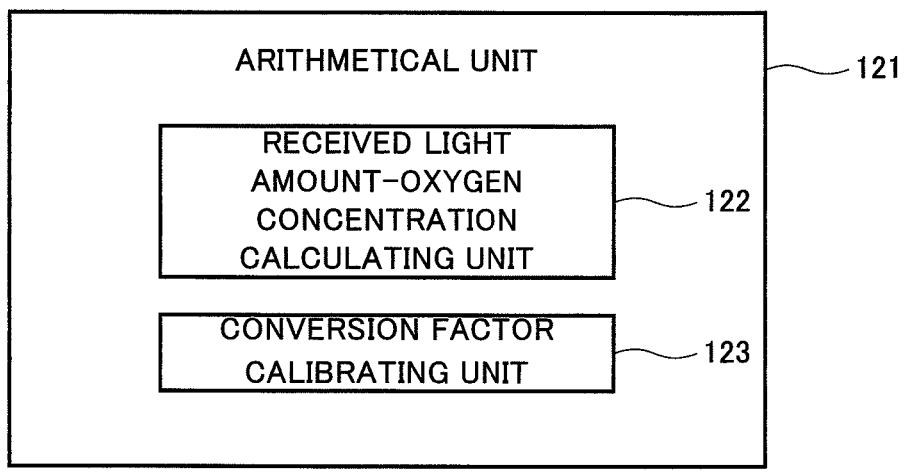
FIG. 12 is a block diagram schematically showing the configuration of an arithmetical unit of the non-destructive inspection device.

As shown in FIG. 12, the non-destructive inspection device 6 includes an arithmetical unit 121. The arithmetical unit 121 includes: a received light amount-oxygen concentration calculating unit 122 that receives a detected value from the laser receiving section 59B, that is, an amount of transmitted laser light as an amount of received light, and determines an oxygen concentration; and a conversion factor calibrating unit 123 that receives the detected values of oxygen concentrations in the two calibration containers 3 and calibrates a conversion factor (also called a sensitivity coefficient) R set for the received light amount-oxygen concentration calculating unit 122.

Figure 13:
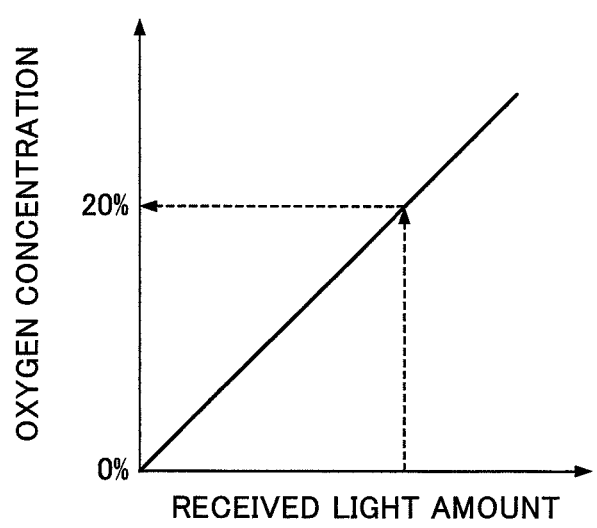
FIG. 13 is a graph showing the relationship between an oxygen concentration and an amount of laser light received for the inspection of the non-destructive inspection device.

For example, as shown in FIG. 13, a graph of the relationship between an amount of received light and an oxygen concentration, that is, the conversion factor R is set for the received light amount-oxygen concentration calculating unit 122. In the conversion factor calibrating unit 123, a current graph, that is, a conversion factor R' is determined based on an amount of received light in the inspection of the two calibration containers 3. As a matter of course, this graph is determined by measuring an amount of light received at a concentration of 0% and an amount of light received at a concentration of 20%. Moreover, oxygen concentrations in the two calibration containers 3 can be properly changed according to the measurement range of a measurement target.

The determined graph, that is, the new conversion factor R' is inputted to the received light amount-oxygen concentration calculating unit 122 and is used thereafter. When the conversion factor hardly changes, the current conversion factor R is naturally used.

The overall operation of the liquid filler, e.g., an inspecting operation will be particularly discussed below.

In this configuration, the containers 1 are moved from the feeding/ejecting machine to the receiving area 5A of the transport path 5 and are sequentially held in groups of three by the container holders 16 provided on the ring plate 15.

In the gas feeding area 5B, nitrogen gas is fed from the inlets 2 into the containers 1. In the subsequent liquid feeding area 5C, a liquid is fed from the inlets 2. After that, the containers 1 are moved to the sealing area 5D to seal the inlets 2 and then the containers 1 are moved to the inspection area 5E to check oxygen concentrations, that is, the quality of the containers 1.

When the three containers 1 are moved to the inspection area 5E, the posture fixing device 29 is first released to tilt the container 1.

Subsequently, the bottom of the container 1 is pressed from both sides by the pressing plates 97 of the container pressing members 88A and 88B in the tilting device 81 disposed below the container 1, moving gas in the container 1 upward. After that, as shown in FIG. 14, the container 1 is tilted in the predetermined direction a by the tilting devices 89A and 89B to move up one of the shoulders 1a. In this state, the three containers 1 are sequentially inspected.

In other words, the inspection tool 60 stopped at the first calibration position (D) is moved to the first inspection position (A).

Figure 9:
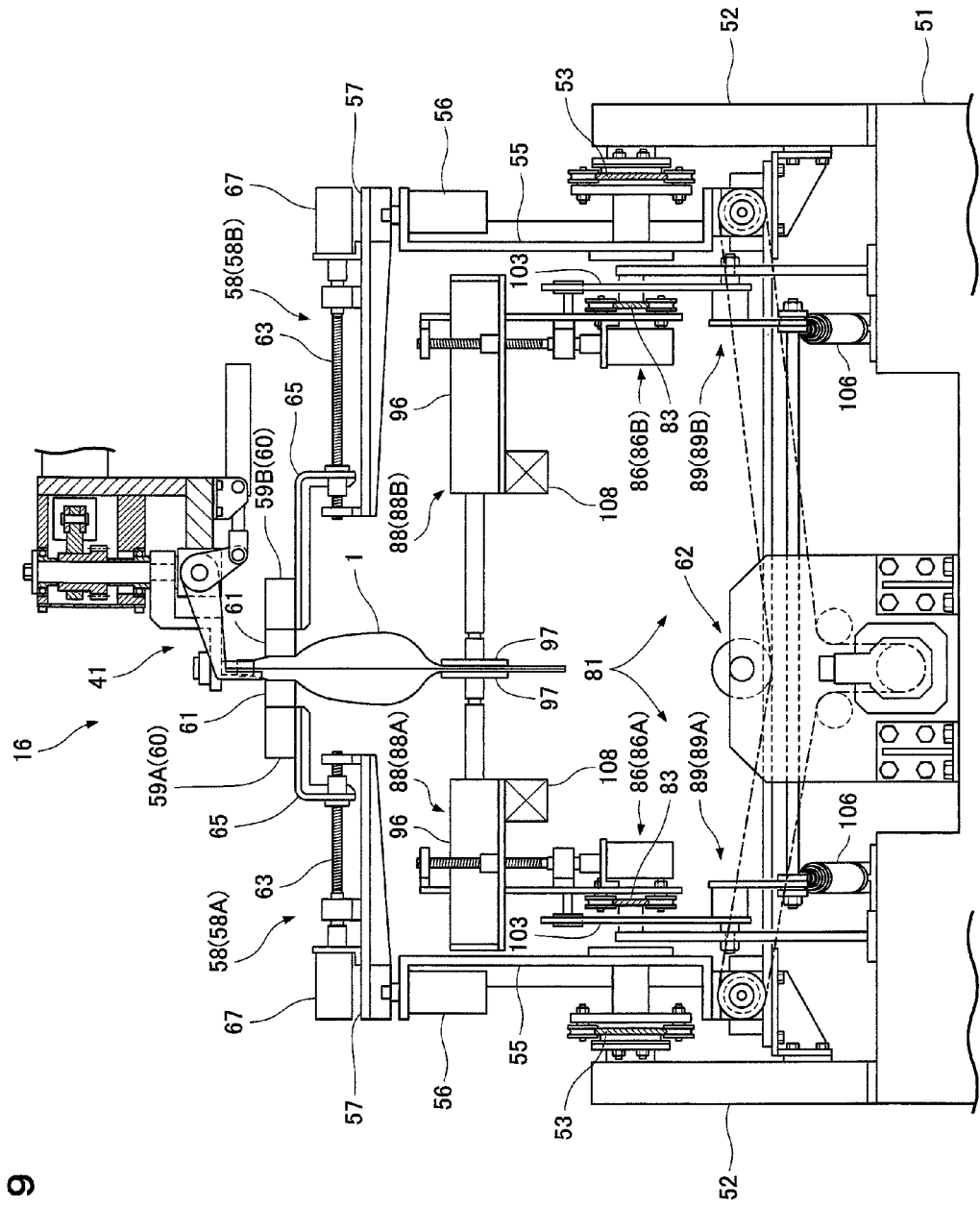
FIG. 9 is a sectional view showing the principle part of the non-destructive inspection device during an inspection.

Then, as shown in FIG. 9, the moving member 65 is protruded to the container 1 by the moving devices 58. In other words, as shown in FIG. 15, the right and left gas-filled chambers 61 are brought close to each other to sandwich the gas phase portion K of the shoulders 1a of the container 1 from both sides with a constant distance. Accordingly, an air layer is removed between the gas-filled chambers 61 and the gas phase portion K of the container 1.

In this state, a laser beam is emitted from the laser emitting section 59A, passes through the container 1, and is received by the laser receiving section 59B.

The arithmetical unit 121 receives the amount of received light, that is, the amount of the transmitted laser beam detected by the laser receiving section 59B. In the arithmetical unit 121, an oxygen concentration is determined based on the amount of the received laser beam (also called an extinction ratio) and then it is decided whether the oxygen concentration is proper or not, in other words, the quality of the container 1 is decided. As a matter of course, a decision unit (not shown) is provided that decides whether an oxygen concentration is proper or not by comparing the oxygen concentration with a set value.

At the completion of the inspection at the first inspection position (A), the laser emitting section 59A and the laser receiving section 59B, that is, the inspection tool 60, are moved to the second inspection position (B) by the moving device 62 and the second container 1 is similarly inspected. After that, the inspection tool 60 is moved to the third inspection position (C) by the moving device 62 and the third container 1 is inspected.

When it is decided that an oxygen concentration in the container 1 is not proper, that is, when the oxygen concentration exceeds a permissible value, it is decided that the container 1 is defective. Thus the container 1 is transported to the defective item ejection area 5G and is ejected to the outside without being covered with a protective film.

At the completion of the inspections of the three containers 1, the tilting device 81 returns the tilted containers 1 from the tilting position to a vertical position. After that, the three containers 1 are fixed by the posture fixing device 29, and then the rotating unit 12 rotates the ring plate 15, and then the subsequent three containers 1 are transported to the inspection area E and undergo inspections.

In the subsequent inspections, the inspection tool 60 is sequentially moved in an opposite direction from the previous inspection to inspect the three containers 1.

When the inspection tool 60 is moved to a calibration position (D or E), the calibration container 3 undergoes the same inspection, that is, a calibrating operation at each position. As a matter of course, the calibration container 3 is rotated about the horizontal axis during the calibrating operation.

The calibrating operation is performed beforehand at a set time, for example, every several hours or at the start of an operation on that day.

An inspection result in the calibration operation is inputted to the conversion factor calibrating unit 123 and calibration is performed on the graph of the relationship between an amount of the received laser beam and an oxygen concentration, that is, the conversion factor R.

As has been discussed, the inert gas chambers on the ends of the laser emitting section and the laser receiving section are filled with nitrogen gas. In this state, the gas phase portion of the container is pressed from both sides to a constant thickness by the ends of the laser emitting section and the laser receiving section, air is removed between the end faces of the laser emitting section and the laser receiving section and the surface of the gas phase portion of the bag-shaped container, and a laser beam is emitted to measure an oxygen concentration. At this point, the bottom of the container is pressed (held) and tilted in the vertical plane by the container pressing member, and then the gas phase portion of the shoulders of the tilted container is measured. This can increase the volume of the gas phase portion so as to move a sufficient amount of oxygen molecules to the shoulder, facilitating measurement of an oxygen concentration with high accuracy.

Moreover, vibrations applied to the bag-shaped container by the vibrator can evenly disperse oxygen molecules, achieving stable and uniform measured values even with a low oxygen concentration.

Furthermore, when the inspection tool is calibrated, the cylindrical calibration container is rotated, achieving precise calibration.

In the present embodiment, the inspection tool 60 is sequentially moved to the three containers 1. For example, the three containers 1 may each have the inspection tool 60 at the inspection position E. In this case, it is needless to say that the inspection tool 60 does not need to be moved.

Figure 16:
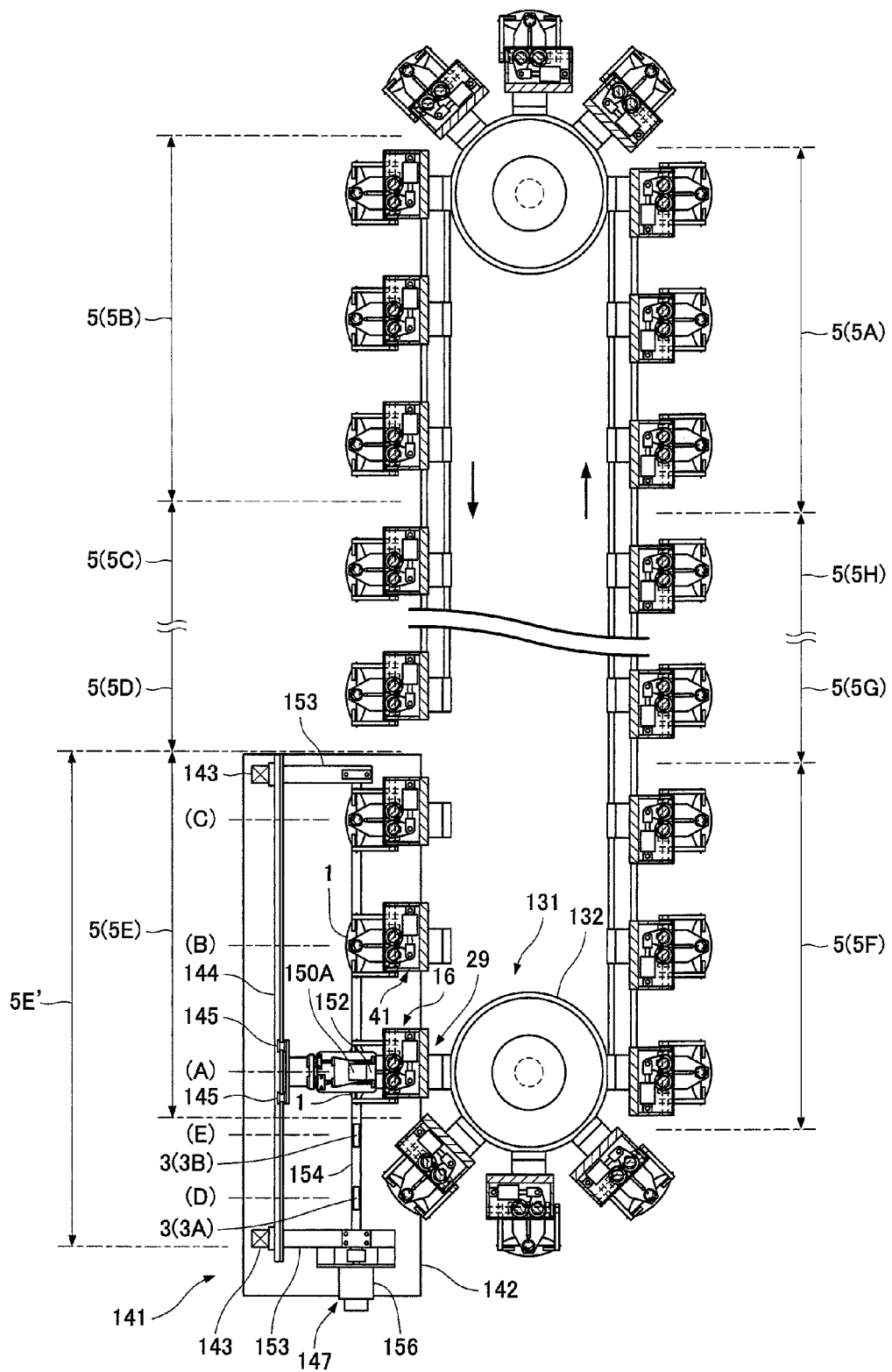
FIG. 16 is a plan view schematically showing the configuration according to a modification of the non-destructive inspection device according to the embodiment of the present invention used for another liquid filler.

In the present embodiment, the transport path 5 of the containers 1 is circular, that is, the rotary type. For example, the transport path 5 may be oval, that is, a linear type, as shown in FIG. 16. Also in this case, the same effect can be achieved as in the present embodiment. The calibration positions (D) and (E) are placed outside the transport path 5 of the containers 1, e.g., outside the semicircular parts of the transport path 5. In this case, the two calibration positions (D, E) are placed outside one of the semicircular parts.

In this case, an oxygen concentration in tilted one of the containers is measured with the inspection tool, allowing the tilting device and the inspection tool to simultaneously move to the inspection positions.

Figure 17:
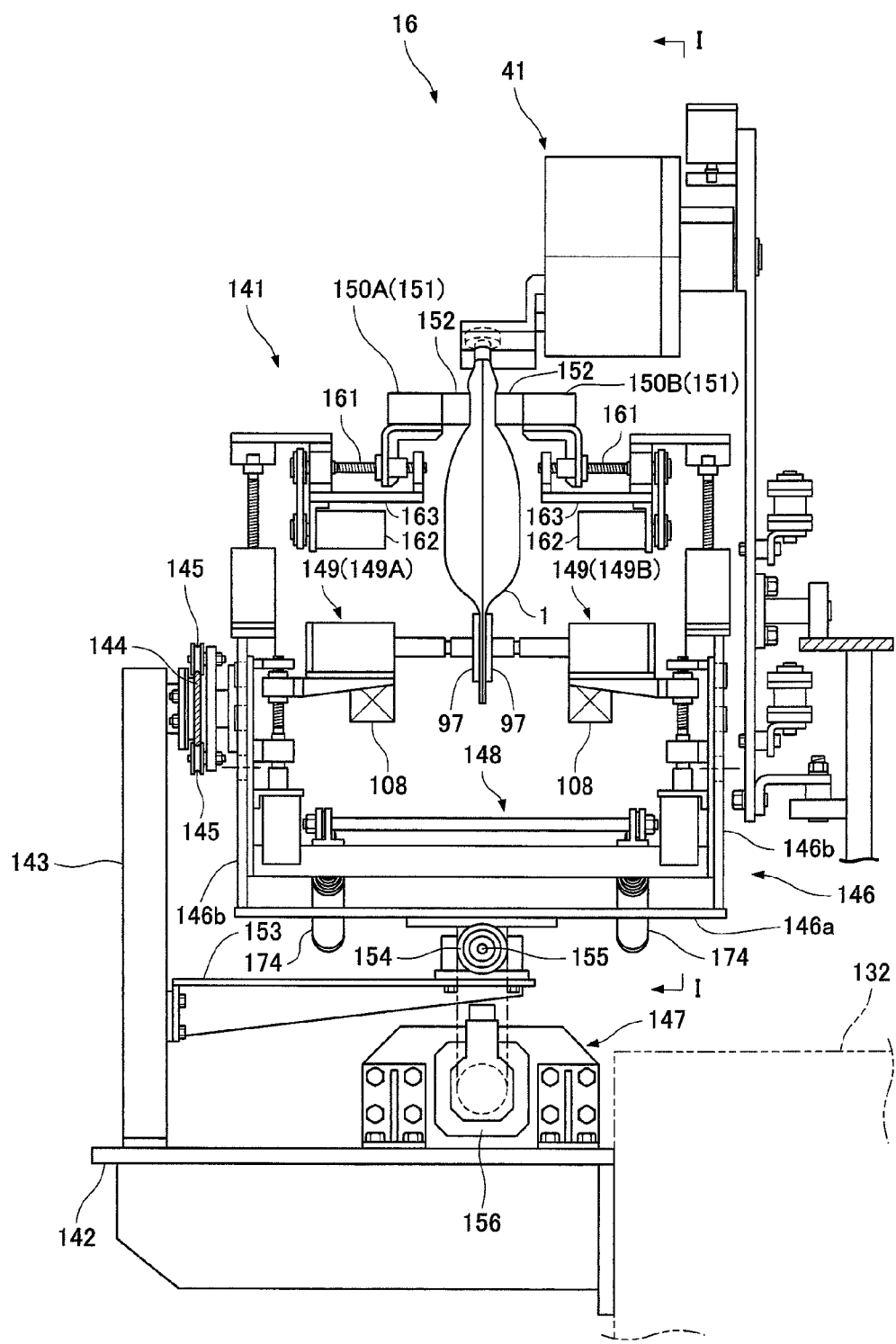
FIG. 17 is a cross-sectional view illustrating the principal part of the non-destructive inspection device according to the modification.
Figure 18:
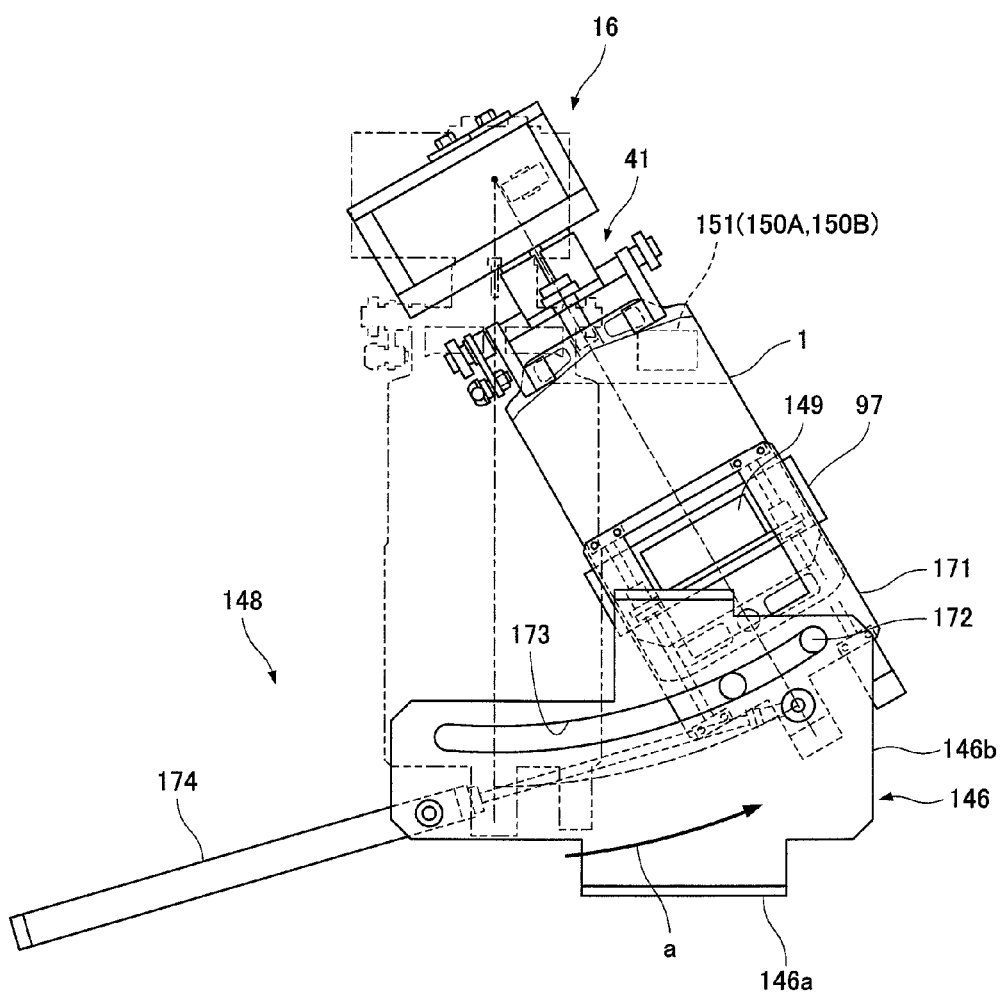
FIG. 18 is an I-I sectional view of FIG. 17.

Referring to FIGS. 16 to 18, a non-destructive inspection device provided for the linear liquid filler will be simply described below.

Specifically, a non-destructive inspection device 141 includes: a support pedestal 142 provided near a casing 132 of a rotating unit 131 in the linear liquid filler; a guide rail 144 that is a guide member horizontally attached to support members 143 raised on the respective outer edges of the support pedestal 142; a movable body 146 that is shaped like a groove (including a bottom plate 146a and side plates 146b raised from the right and left sides of the bottom plate 146a) in front view (longitudinal section) and is guided by upper and lower guide wheels 145 on the guide rail 144; a moving device 147 that moves the movable body 146 in a predetermined direction (longitudinally, that is, the transport direction of a container at the inspection position); a container pressing member 149 (149A, 149B) that is provided on the movable body 146 so as to tilt in a predetermined direction a via a tilting device 148 and press (hold) the lower part of a container 1; a laser emitting section 150A and a laser receiving section 150B that serve as an inspection tool 151 of the container 1 provided in the movable body 146 and above the container pressing member 149; and gas-filled chambers 152 provided on the emitting section 150A and the receiving section 150B.

The moving device 147 includes: a pair of front and rear support brackets 153 projected from the lower parts of the support members 143 to an inspection path; a rotary screw shaft 155 that is provided on the front and rear support brackets 153 in the longitudinal direction so as to rotate about the axis of the rotary screw shaft 155 and is screwed into a nut member (having a ball screw mechanism) 154 provided under the bottom plate 146a of the movable body 146; and a motor 156 that rotates the rotary screw shaft 155 via a pulley, a transmission belt, and so on. Thus, the motor 156 rotating the rotary screw shaft 155 can sequentially move the movable body 146, that is, the inspection tool 151 and the container pressing member 149 at the same time to the inspection positions (A, B, C) and the calibration positions (D, E).

The container pressing member 149 is configured as in the embodiment and thus the explanation thereof is omitted.

For the inspection tool 60 in the rotary device according to the foregoing embodiment, the motor 67 for rotating the rotary screw shaft 63 is disposed above the lift plate 57, whereas for the inspection tool 151 of the linear type, a motor 162 for rotating a rotary screw shaft 161 is disposed below a lift plate 163 on which the inspection tool 151 is disposed.

The tilting device 81 in the rotary device according to the foregoing embodiment simultaneously tilts the three containers 1, whereas as shown in FIG. 18, the tilting device 148 of the linear type tilts the single container 1.

The basic structure of the tilting device 148 is identical to that of the foregoing embodiment. The tilting device 148 is specifically different in that guide rollers 172 provided on a tilted plate 171 are guided by, instead of a guide rail, an arc-shaped guide groove 173 formed on the side plate 146b of the movable body 146. Needless to say, tilting cylinders 174 for tilting the tilted plate 171 are supported near the movable body 146, for example, by the side plates 146b.

As shown in FIG. 16, a calibration container 3 at the calibration position (D, E) can rotate about the horizontal axis as in the foregoing embodiment.

In the configuration, in measurement of an oxygen concentration in the container 1, the postures of the containers 1 moved to the three inspection positions (A, B, C) are released from the fixed postures by a posture fixing device (29) of the containers 1 at each position.

Specifically, the moving device 147 moves the movable body 146 to the inspection position (A), the bottom of the container 1 is pressed by pressing plates (97), and then the container 1 is tilted in the predetermined direction a by the tilting device 148, thereby moving gas to shoulders 1a.

Moreover, the inspection tool 151, that is, the gas-filled chambers 152 provided on the laser emitting section 150A and the laser receiving section 150B come into contact with the shoulders 1a of the container 1, allowing measurement of an oxygen concentration in a gas phase portion K of the container 1. Needless to say, the container 1 is vibrated by vibrators (108) during the measurement. Reference numerals (numbers) in parentheses indicate the same members as in the foregoing embodiment, and thus the members are denoted by the same numbers.

Hence, the linear type can achieve the same operation and effect as the rotary type.

In the foregoing embodiments, the right and left gas-filled chambers are brought close to each other so as to hold the gas phase portion at the shoulders of the bag-shaped container from both sides with a predetermined distance. While the right and left gas-filled chambers are brought close to each other with a certain distance (constant distance), the bottom of the bag-shaped container may be held by the right and left pressing plates so as to expand the shoulders, allowing the surfaces of the shoulders to come into contact with the right and left gas-filled chambers. In other words, the amounts of travel of the pressing plates are controlled so as to bring the surface of the bag-shaped container into contact with the surfaces of the right and left gas-filled chambers close to each other. Thus, the right and left gas-filled chambers moved to predetermined positions with a certain distance are not subjected to a reaction force from the bag-shaped container, keeping a constant distance between the right and left gas-filled chambers throughout measurement. This leads to higher measuring accuracy.

The invention claimed is:

1. A non-destructive inspection device for an oxygen concentration in a bag-shaped container, the non-destructive inspection device being provided in a liquid filler for feeding a liquid into the bag-shaped containers held by container holders on a transport unit and transported along a transport path including at least a liquid filling area, a sealing area, and an inspection area, the non-destructive inspection device emitting, in the inspection area of the transport path, a laser beam to a gas phase portion of the bag-shaped container filled with the liquid and measuring an oxygen concentration in the bag-shaped container based on an amount of transmitted light, the non-destructive inspection device including: a pair of right and left moving members provided on the right and left of the inspection area of the transport path such that the moving members are moved toward and away from the bag-shaped container by a moving device; a laser emitting section that is provided on one of the moving members and emits the laser beam for measuring the oxygen concentration; and a laser receiving section that is provided on the other moving member and receives the laser beam, wherein the non-destructive inspection device further includes:

translucent inert gas chambers having an equal length on respective end faces of the laser emitting section and the laser receiving section; and a tilting device that is disposed on the right and left of the inspection area of the transport path so as to press the bag-shaped container from both sides by means of a container pressing member and tilt the container in a vertical plane, the container being held by the container holder so as to pivot in the vertical plane, and in measurement of the oxygen concentration in the inspection area, the tilting device tilts the bag-shaped container to a predetermined angle and brings the pair of right and left moving members close to each other at shoulders of an upper part of the tilted bag-shaped container so as to bring the end faces of the laser emitting section and the laser receiving section into contact with a surface of the gas phase portion of the bag-shaped container, keeping a constant thickness of the gas phase portion while evacuating air between the end faces of the laser emitting section and the laser receiving section and the surface of the gas phase portion of the bag-shaped container.

2. The non-destructive inspection device for an oxygen concentration in a bag-shaped container according to claim 1, wherein the container pressing member comprises a vibrator.

3. The non-destructive inspection device for an oxygen concentration in a bag-shaped container according to claim 1, wherein the transport unit is stopped and the pair of moving members having the laser emitting section and the laser receiving section is sequentially movable to the stopped bag-shaped containers in inspections of the bag-shaped containers.

4. The non-destructive inspection device for an oxygen concentration in a bag-shaped container according to claim 1, further comprising two calibration containers that are made of a translucent material outside the inspection area and are filled beforehand with inert gas having different oxygen concentrations, wherein the pair of moving members having the laser emitting section and the laser receiving section is movable to calibration positions for measuring the oxygen concentrations in the calibration containers.

5. The non-destructive inspection device for an oxygen concentration in a bag-shaped container according to claim 4, wherein the calibration container is conical or cylindrical.

6. The non-destructive inspection device for an oxygen concentration in a bag-shaped container according to claim 5, wherein the calibration container is rotatable about an axis of the container.

7. The non-destructive inspection device for an oxygen concentration in a bag-shaped container according to claim 1, wherein the transport path is circular or oval.

* * * * *